United States Patent [19]

Gehring et al.

[11] Patent Number: 4,734,125

[45] Date of Patent: Mar. 29, 1988

[54] 5-ACYLAMIDO-1-ARYL-PYRAZOLES, COMPOSITION CONTAINING THEM AND HERBICIDAL METHOD OF USING THEM

[75] Inventors: Reinhold Gehring, Wuppertal; Otto Schallner, Monheim; Jörg Stetter, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 1,471

[22] Filed: Jan. 8, 1987

[30] Foreign Application Priority Data

Jan. 15, 1986 [DE] Fed. Rep. of Germany ....... 3600950

[51] Int. Cl.[4] .................... A01N 43/56; C07D 231/38

[52] U.S. Cl. ........................................ 71/92; 71/93; 544/209; 544/212; 544/216; 544/217; 544/218; 544/219; 544/238; 544/298; 544/300; 544/310; 544/316; 544/317; 544/318; 544/319; 544/320; 544/321; 544/405; 546/256; 546/279

[58] Field of Search ............... 548/362, 376, 377, 375; 546/279, 256; 71/92, 93; 544/209, 212, 216, 217, 218, 219, 238, 298, 300, 310, 316, 317, 318, 319, 320, 321, 405

[56] References Cited

FOREIGN PATENT DOCUMENTS 3226513 2/1983 Fed. Rep. of Germany .......... 71/92

*Primary Examiner*—Henry R. Jiles
*Assistant Examiner*—Kurt G. Briscoe
*Attorney, Agent, or Firm*—Sprung Horn Kramer & Woods

[57] ABSTRACT

Herbicidally active 5-acylamido-1-aryl-pyrazoles of the formula

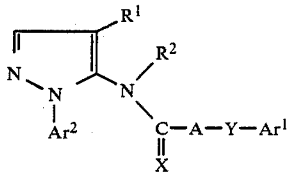

in which $R^1$ represents hydrogen, halogen or nitro, $R^2$ represents hydrogen or alkyl, X represents oxygen or sulphur, Y represents oxygen, sulphur, a sulphinyl group or a sulphonyl group, A represents a straight-chain or branched, optionally substituted alkylene bridge, $Ar^1$ represents in each case optionally substituted aryl or heteroaryl, and $Ar^2$ represents in each case optionally substituted phenyl or pyridyl.

11 Claims, No Drawings

5-ACYLAMIDO-1-ARYL-PYRAZOLES, COMPOSITION CONTAINING THEM AND HERBICIDAL METHOD OF USING THEM

The invention relates to novel 5-acylamido-1-aryl-pyrazoles, several processes for their preparation and their use as herbicides.

It is already known that certain 5-acylamido-1-aryl-pyrazoles, such as, for example, 4-cyano-5-propionamido-1-(2,4,6-trichlorophenyl)-pyrazole, possess herbicidal properties (cf., for example, DE-OS (German Published Specification) No. 3,226,513).

The herbicidal action, against weeds, of these previously known compounds is, however, not always completely satisfactory in all areas of application, as is their compatibility toward important culture plants.

Novel 5-acylamido-1-aryl-pyrazoles of the general formula (I)

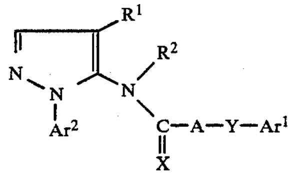

(I)

in which $R^1$ represents hydrogen, halogen or nitro, $R^2$ represents hydrogen or alkyl, X represents oxygen or sulphur, Y represents oxygen, sulphur, a sulphinyl group or a sulphonyl group, A represents a straight-chain or branched, optionally substituted alkylene bridge, $Ar^1$ represents in each case optionally substituted aryl or heteroaryl and $Ar^2$ represents in each case optionally substituted phenyl or pyridyl, have been found.

It has furthermore been found that the novel 5-acylamido- 1-aryl-pyrazoles of the formula (I)

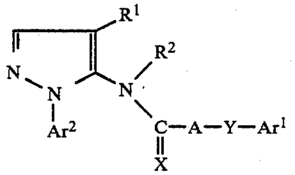

(I)

in which $R^1$ represents hydrogen, halogen or nitro, $R^2$ represents hydrogen or alkyl, X represents oxygen or sulphur, Y represents oxygen, sulphur, a sulphinyl group or a sulphonyl group, A represents a straight-chain or branched, optionally substituted alkylene bridge, $Ar^1$ represents in each case optionally substituted aryl or heteroaryl and $Ar^2$ represents in each case optionally substituted phenyl or pyridyl, are obtained with the aid of the processes described below:

(a) 5-acylamido-1-aryl-pyrazoles of the formula (Ia),

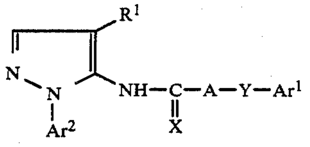

(Ia)

in which $R^1$, X, Y, A, $Ar^1$ and $Ar^2$ have the abovementioned meaning, are obtained when 5-amino-1-aryl-pyrazoles of the formula (II)

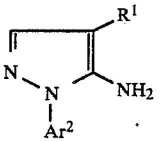

(II)

in which $R^1$ and $Ar^2$ have the abovementioned meaning, are reacted with acylating agents of the formula (III),

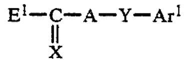

(III)

in which

X, Y, A and $Ar^1$ have the abovementioned meaning and $E^1$ represents an electron-withdrawing leaving group, if appropriate in the presence of a diluent, if appropriate in the presence of an acid acceptor and if appropriate in the presence of a catalyst;

(b) 5-acylamido-1-aryl-pyrazoles of the formula (Ib)

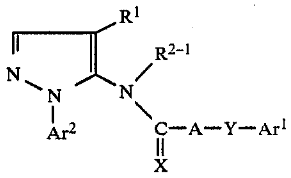

(Ib)

in which $R^1$, X, Y, A, $Ar^1$ and $Ar^2$ have the abovementioned meaning and $R^{2-1}$ represents alkyl, are obtained when the 5-acylamido-1-aryl-pyrazoles of the formula (Ia),

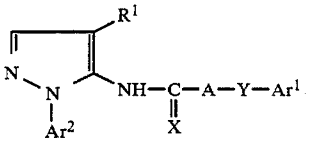

(Ia)

in which $R^1$, X, Y, A, $Ar^1$ and $Ar^2$ have the abovementioned meaning, which are obtained by process (a) are reacted with alkylating agents of the formula (IV), $$E^2—R^{2-1} \quad (IV)$$

in which $R^{2-1}$ has the abovementioned meaning and $E^2$ represents halogen, optionally substituted alkoxysulphonyloxy or optionally substituted arylsulphonyloxy, sulphonyloxy, if appropriate in the presence of a diluent and if appropriate in the presence of an acid acceptor, and also if appropriate in the presence of a catalyst;

(c) 5-acylamido-1-aryl-pyrazoles of the formula (I) are obtained when 5-acylamido-1-aryl-pyrazoles of the formula (V)

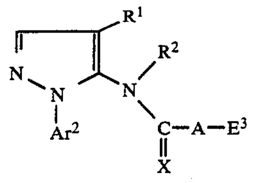
(V)

in which $R^1$, $R^2$, X, A and $Ar^2$ have the abovementioned meaning and $E^3$ represents halogen, are reacted with phenol or thiophenol derivatives of the formula (VI)

$Ar^1$—Y—Z (VI)

in which $Ar^1$ and Y have the abovementioned meaning and

Z represents hydrogen or one equivalent of an alkaline earth metal cation or alkali metal cation, if appropriate in the presence of a diluent and if appropriate in the presence of an acid acceptor and if appropriate in the presence of a suitable catalyst;

(d) 5-acylamido-1-aryl-pyrazoles of the formula (Ic)

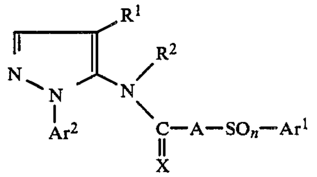
(Ic)

in which $R^1$, $R^2$, X, A, $Ar^1$ and $Ar^2$ have the abovementioned meaning and n represents a number 1 or 2, are obtained when the 5-acylamido-1-aryl-pyrazoles of the formula (Id),

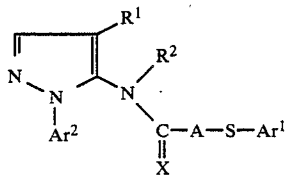
(Id)

in which $R^1$, $R^2$, X, A, $Ar^1$ and $Ar^2$ have the abovementioned meaning, which are obtained with the aid of the processes (a), (b) or (c), are reacted with oxidizing agents of the formula (VII), $R^3$—O—O—H (VII)

in which $R^3$ represents hydrogen or in each case optionally substituted alkanoyl or aroyl, if appropriate in the presence of a diluent and if appropriate in the presence of an acid acceptor and also if appropriate in the presence of a catalyst;

(e) 5-acylamido-1-aryl-pyrazoles of the formula (Ie)

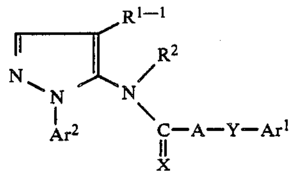
(Ie)

in which $R^2$, X, A, Y, $Ar^1$ and $Ar^2$ have the abovementioned meaning and $R^{1-1}$ represents halogen or nitro, are obtained when the 5-acylamido-1-aryl-pyrazoles of the formula (If),

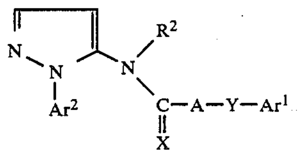
(If)

in which $R^2$, X, Y, A, $Ar^1$ and $Ar^2$ have the abovementioned meaning, which are obtained with the aid of the processes (a), (b), (c) or (d), are reacted with halogenating or nitrating agents of the formula (VIII), $R^{1-1}$ —$E^4$ (VIII)

in which $R^{1-1}$ has the abovementioned meaning and $E^4$ represents an electron-withdrawing leaving group, if appropriate in the presence of a diluent and if appropriate in the presence of a catalyst or reaction auxiliary.

Finally, it has been found that the novel 5-acylamido-1-aryl-pyrazoles of the general formula (I) have herbicidal, and, in particular, also selective herbicidal, properties.

Surprisingly, the 5-acylamido-1-aryl-pyrazoles of the general formula (I) according to the invention display a considerably better general herbicidal action against problem weeds which are difficult to combat, and simultaneously display a markedly improved compatibility toward important culture plants in comparison to the 5-acylamido1-aryl-pyrazoles which are known from the state of the art, such as, for example, 4-cyano-5-propionamido-1-(2,4,6-trichlorophenyl)-pyrazole, which are similar compounds chemically and regarding their action.

The 5-acylamido-1-aryl-pyrazoles according to the invention are generally defined by the formula (I). Preferred are compounds of the formula (I) in which $R^1$ represents hydrogen, nitro, fluorine, chlorine, bromine or iodine, $R^2$ represents hydrogen or straight-chain or branched alkyl having 1 to 12 carbon atoms, X represents oxygen or sulphur, Y represents oxygen, sulphur, a sulphinyl or a sulphonyl group, A represents a straight-chain or branched, optionally singly or multiply, identically or differently, halogen-substituted alkylene bridge having 1 to 6 carbon atoms, $Ar^1$ represents in each case optionally singly or multiply, identically or differently substituted phenyl, 2-pyridyl, 3-pyridyl, 4-pyridyl, 2-pyrimidyl, 4-pyrimidyl, 5-pyrimidyl, 3-pyridazinyl, 4-pyridazinyl, pyrazinyl or s-triazinyl, suitable substituents in each case being: halogen, cyano, nitro, in each case straight-chain or branched alkyl, alkoxy or alkoxycarbonyl having 1 to 4 carbon atoms in each of the alkyl parts, in each case straight-chain or branched haloalkyl or haloalkoxy having 1 to 4 carbon atoms and 1 to 9 identical or different halogen atoms in each case, or a $-S(0)_m-R^4$ radical, where $R^4$ represents amino, in each case straight-chain or branched alkyl, alkylamino, dialkylamino or haloalkyl having 1 to 4 carbon atoms in each of the individual alkyl parts and, in the case of haloalkyl, having 1 to 9 identical or different halogen atoms and m represents a number 0, 1 or 2, and $Ar^2$ represents in each case optionally singly or multiply, identically or differently, substituted phenyl, 2-pyridyl, 3-pyridyl or 4-pyridyl, suitable substituents in each case being those mentioned for $Ar^1$.

Particularly preferred are 5-acylamide-1-aryl-pyrazoles of the formula (I) in which $R^1$ represents hydrogen, nitro, chlorine or bromine, $R^2$ represents hydrogen or straight-chain or branched alkyl having 1 to 8 carbon atoms, X represents oxygen or sulphur, Y represents oxygen, sulphur, a sulphinyl group or a sulphonyl group, A represents a bridging member of the formula $$-CH_2-;\ -CH_2-CH_2-;\ -\underset{CH_3}{\underset{|}{CH}}-;\ -CCl_2-CH_2-;$$

$$-CHCl-CH_2-;\ -\underset{CH_3}{\underset{|}{CH}}-CH_2-;\ -CH_2-CH_2-CH_2-;$$

$$-CH_2-CH_2-CH_2-CH_2-;\ -\overset{CH_3}{\overset{|}{\underset{CH_3}{\underset{|}{C}}}}-CH_2-;\ -\underset{Br}{\underset{|}{CH}}-CH_2-\text{ or}$$

$$-CBr_2-CH_2-,$$

$Ar^1$ represents in each case optionally singly to triply, identically or differently, substituted phenyl, 2-pyridyl, 3-pyridyl, 4-pyridyl, 2-pyrimidyl, 4-pyrimidyl, 5-pyrimidyl, 3-pyridazinyl, 4-pyridazinyl, pyrazinyl or s-triazinyl, suitable substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, tifluorodichloroethyl, pentachloroethyl, trifluoromethoxy, trichloromethoxy, dichlorofluoromethoxy, difluorochloromethoxy, chloromethoxy, dichlorometh bxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a $-S(O)_m-R^4$ radical, where $R^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents a number 0, 1 or 2,and $Ar^2$ represents optionally singly to quintuply, identically or differently, substituted phenyl or in each case optionally singly to quadruply, identically or differently, substituted 2-pyridyl or 4-pyridyl, suitable substituents in each case being those mentioned for $Ar^1$.

Very particularly preferred are 5-acylamido-1-aryl-pyrazoles of the general formula (I) in which $R^1$ represents hydrogen or nitro, $R^2$ represents hydrogen, methyl or ethyl, X represents oxygen or sulphur, Y represents oxygen, sulphur, a sulphinyl group or a sulphonyl group, A represents a bridging member of the formula $$-CH_2-;\ -CH_2-CH_2-;\ -CH_2-CH_2-CH_2-;\ -\underset{CH_3}{\underset{|}{CH}}-;$$

$$-\underset{CH_3}{\underset{|}{CH}}-CH_2-;\ -\overset{CH_3}{\overset{|}{\underset{CH_3}{\underset{|}{C}}}}-CH_2-;\ -\overset{Cl}{\overset{|}{CH}}-CH_2-;\ -\overset{Br}{\overset{|}{CH}}-CH_2-\text{ or}$$

$$-CCl_2-CH_2-,$$

$Ar^1$ represents in each case optionally singly to triply, identically or differently, substituted phenyl, 2-pyridyl, 4-pyridyl, 2-pyrimidyl, 4-pyrimidyl, 5-pyrimidyl or s-triazinyl, suitable substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a $-S(0)_m-R^4$ radical, where $R^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents a number 0, 1 or 2, and $Ar^2$ represents optionally singly to quintuply, identically or differently, substituted phenyl or optionally singly to quadruply, identically or differently, substituted 2-pyridyl, suitable substituents in each case being: fluorine, chlorine, bromine, methyl, ethyl, n-i-propyl, trifluoromethyl, difluorochloromethyl, fluorodichloromethyl, trifluoromethoxy or a $-S(O)_p-R^5$ radical, where $R^5$ represents methyl, difluorochloromethyl, dichlorofluoromethyl, trifluoromethyl, amino, dimethylamino or diethylamino and represents a number 0, 1 or 2.

Apart from the compounds mentioned in the case of the preparation examples, the following 5-acylamido-1-aryl-pyrazoles of the general formula (I) may be mentioned individually:

TABLE 1

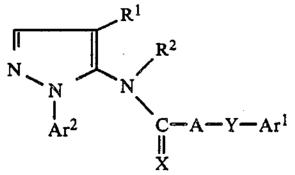

(I)

| $R^1$ | $R^2$ | 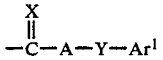 | $Ar^2$ |
|---|---|---|---|
| H | H | 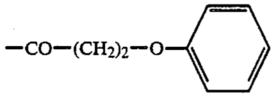 | 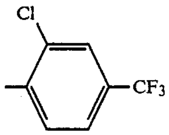 |
| $NO_2$ | H | 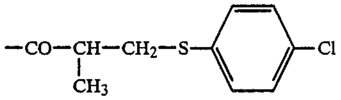 | 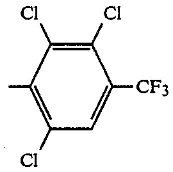 |
| $NO_2$ | $CH_3$ | 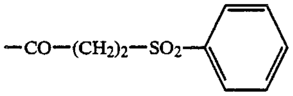 | 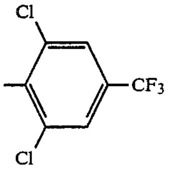 |
| H | $CH_3$ | 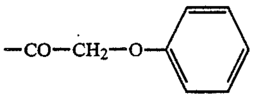 | 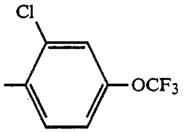 |
| $NO_2$ | H | 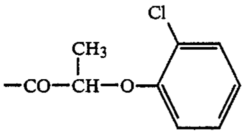 | 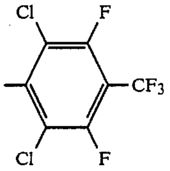 |
| $NO_2$ | H | 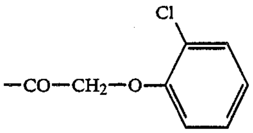 | 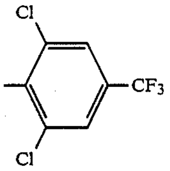 |
| $NO_2$ | H | 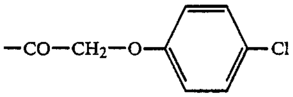 | 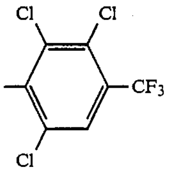 |

TABLE 1-continued
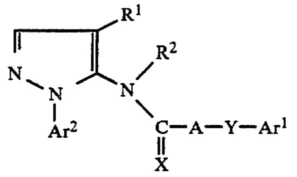
(I)
| $R^1$ | $R^2$ | $-\overset{\overset{X}{\|}}{C}-A-Y-Ar^1$ | $Ar^2$ |
|---|---|---|---|
| $NO_2$ | H | 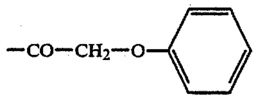 | 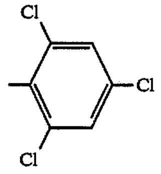 |
| $NO_2$ | H | 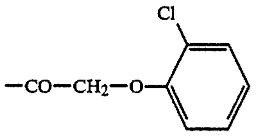 | 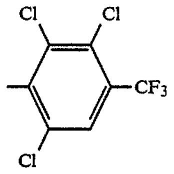 |
| $NO_2$ | H | 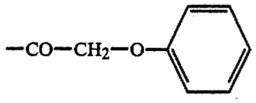 | 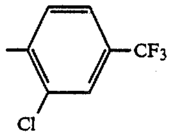 |
| $NO_2$ | H | 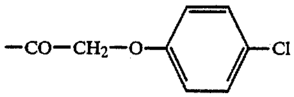 | 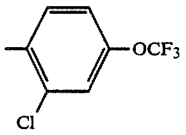 |
| $NO_2$ | H | 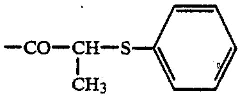 | 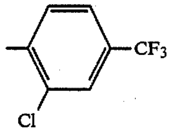 |
| $NO_2$ | H | 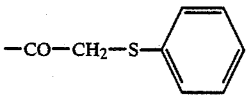 | 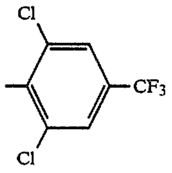 |
| $NO_2$ | H | 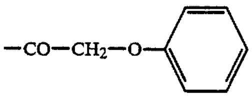 | 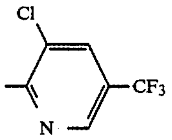 |
| $NO_2$ | H | 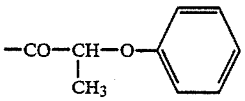 | 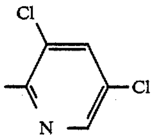 |

TABLE 1-continued (I)

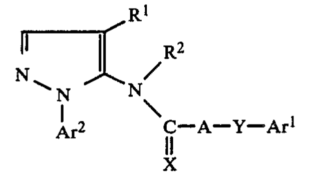

| $R^1$ | $R^2$ | 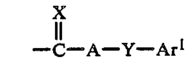 | $Ar^2$ |
|---|---|---|---|
| $NO_2$ | H | 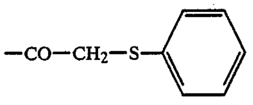 | 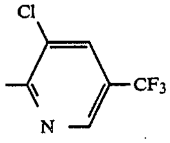 |
| $NO_2$ | H | 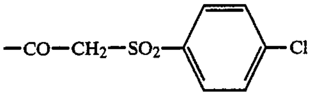 | 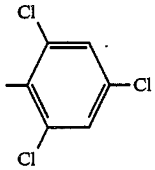 |
| $NO_2$ | H | 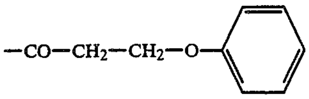 | 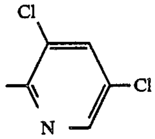 |
| $NO_2$ | H | 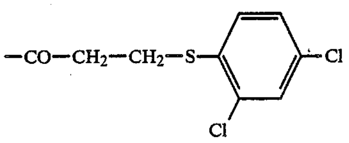 | 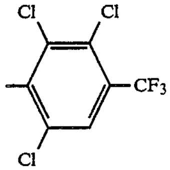 |

If, for example, 5-amino-4-nitro-1-(2,6-dichloro-4-trifluoromethyl-phenyl)-pyrazole and 3-phenylsulphonyl-propionyl chloride are used as starting materials, then the course of the reaction of the process (a) according to the invention can be represented by the following equation:

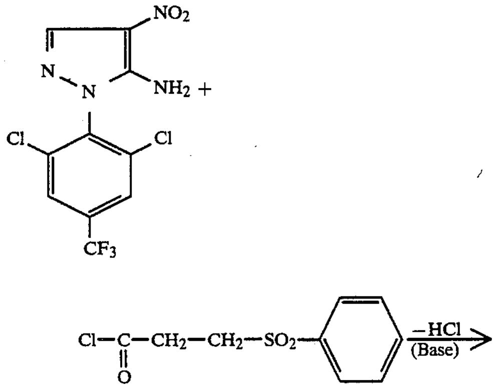

-continued

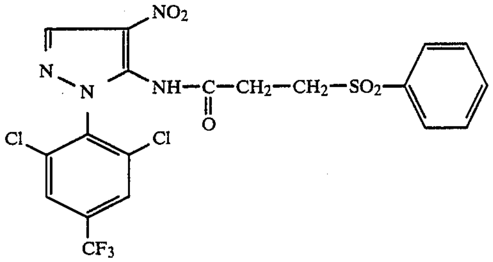

If, for example, 5-phenoxyacetamido-1-(2,3,6-trichloro-4-trifluoromethyl-phenyl)-pyrazole and dimethyl sulphate are used as starting materials, then the course of the reaction of the process (b) according to the invention can be represented by the following equation:

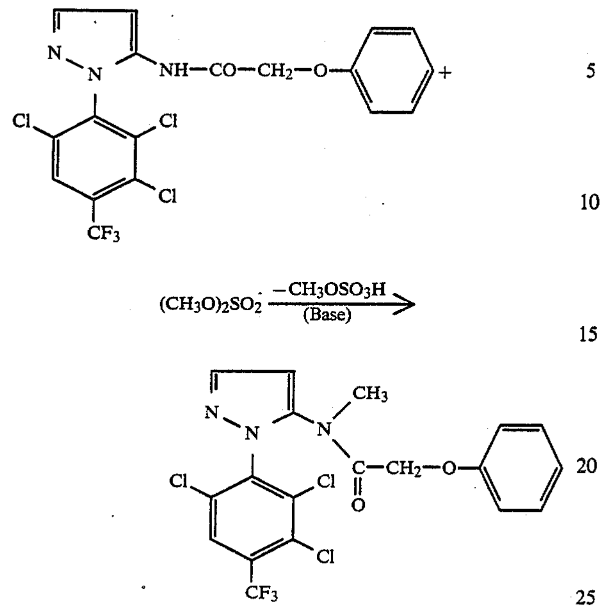

If, for example, 5-(3-chloropropionamino)-4-nitro-1-(2-chloro-4-trifluoromethyl-phenyl)-pyrazole and thiophenol are used as starting materials, then the course of the reaction of the process (c) according to the invention can be represented by the following equation:

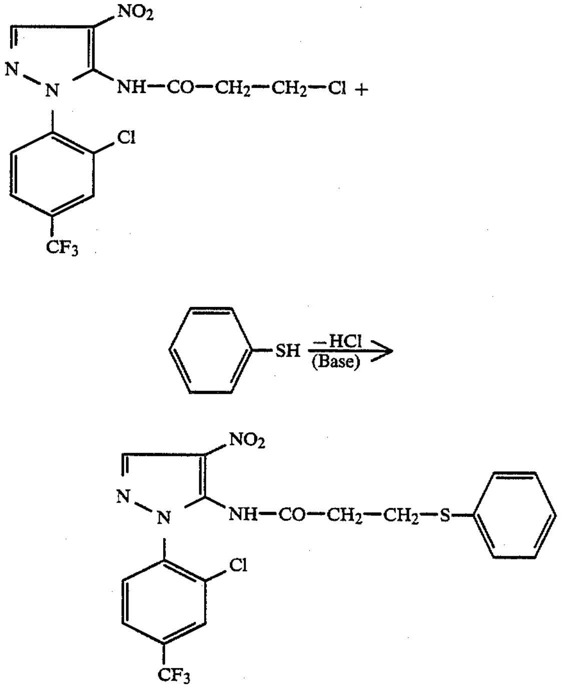

If, for example, 5-phenylthioacetamido-4-nitro-1(2-chloro-4-trifluoromethoxy-phenyl)-pyrazole is used as the starting compound and 3-chloroperbenzoic acid is used as oxidizing agent, then the course of the reaction of the process (d) according to the invention can be represented by the following equation:

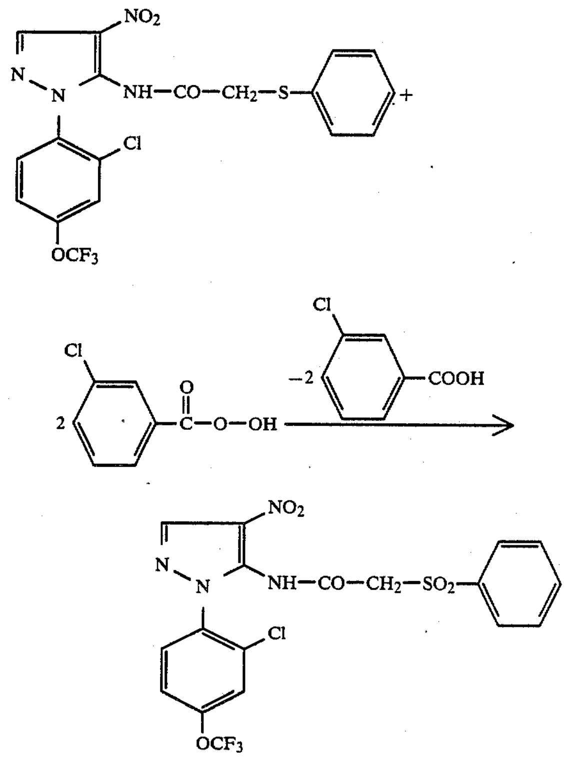

If, for example, 5-(2-phenoxypropionamido)-1-(2,6-dichloro-4-trifluoromethylthio-phenyl)-pyrazole and nitric acid are used as starting materials, then the course of the reaction of the process (e) according to the invention can be represented by the following equation:

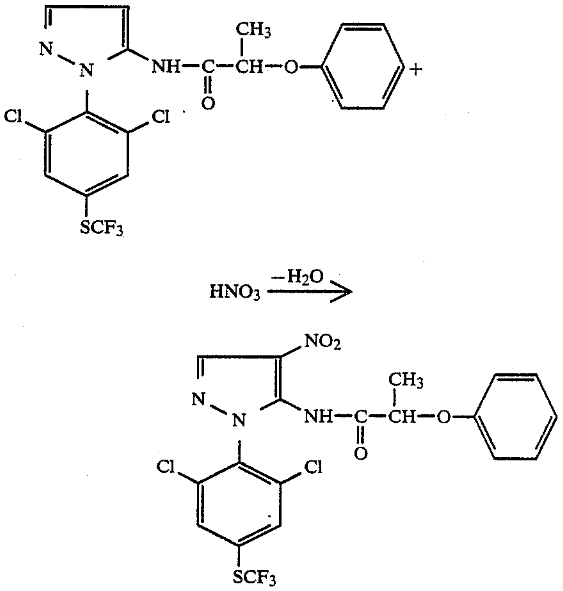

The 5-amino-1-aryl-pyrazoles required as starting materials for carrying out the process (a) according to the invention are generally defined by the formula (II). In this formula (II), $R^1$ and $Ar^2$ preferably represent those radicals which have already been mentioned in connection with the description of the substances, according to the invention, of the formula (I) as being preferred for these substituents.

Some of the 5-amino-1-aryl-pyrazoles of the formula (II) are known (cf., for example, U.S. Pat. No. 4,614,533 issued Sept. 30, 1986) some are the subject material of our own previous non-published German patent application DE-P No. 3,520,330 of June 7, 1985 corresponding to U.S. application Ser. No. 866,638 filed May 22, 1986, now pending, and can be obtained analogously to known processes (cf. U.S. Pat. No. 4,614,533, supra), for example when arylhydrazines of the formula (IX), $Ar^2—NH—NH_2$ (IX)

in which $Ar^2$ has the abovementioned meaning, are reacted with 2-haloacrylonitriles of the formula (X),

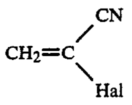

(X)

in which Hal represents halogen, particularly chlorine or bromine, either initially in a 1st stage, if appropriate in the presence of a diluent, such as, for example, glacial acetic acid or ethanol, and also if appropriate in the presence of a reaction auxiliary, such as, for example, sodium acetate, at temperatures between −20° C. and +20° C. to give the arylhydrazine derivatives of the formula (XI),

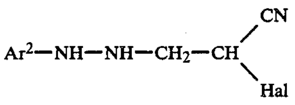

(XI)

in which $Ar^2$ and Hal have the abovementioned meaning, and cyclizing this in a 2nd stage, if appropriate in the presence of a diluent, such as, for example, ethylene glycol monoethyl ether, and if appropriate in the presence of an acidic catalyst, such as, for example, sulphuric acid or phosphoric acid, at temperatures between +50° C. and +150°C., or cyclizing directly in one reaction step without isolation of the intermediate of the formula (XI), if appropriate in the presence of a diluent, such as, for example, ethylene glycol monoethyl ether or ethanol, at temperatures between +50° C. and +150° C., and nitrating the 4-unsubstituted 5-amino-1-aryl-pyrazoles of the formula (IIa)

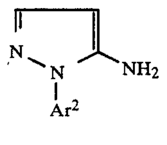

(IIa)

in which $Ar^2$ has the abovementioned meaning, which can be thus obtained, in a subsequent reaction using a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C., or, alternatively, halogenating using a halogenating agent, such as, for example, chlorine, sulphuryl chloride, phosphorus pentachloride, N-chlorosuccinimide, bromine, phosphorus tribromide or N-bromosuccinimide, if appropriate in the presence of a diluent, such as, for example, methylene chloride or glacial acetic acid, and if appropriate in the presence of a reaction auxiliary, such as, for example, boron trifluoride, at temperatures between −20° C. and +50° C.

In this reaction, it can, under certain circumstances, be advantageous to protect the amino group in the 5-position of the pyrazole ring with the aid of a conventional protecting group technique, for example by acylation, before the halogenation or nitration reaction, and to cleave the amino-protecting group off again after the completed halogenation or nitration, likewise in a conventional manner, for example by saponification using aqueous or alcoholic base.

The arylhydrazines (IX) are known (cf., for example, U.S. Pat. Nos. 4,127,575; 3,609,158; DE-OS (German published specification) No. 2,558,399; J. Chem. Soc. C. 1971, (167–174) or can be obtained by known processes in a simple analogous fashion (cf., for example, Houben-Weyl "Methoden der organischen Chemie [Methods of Organic Chemistry]" Volume X/2, p. 203, Thieme Verlag Stuttgart 1967; U.S. Pat. No. 4,614,533, supra).

The haloacrylonitriles of the formula (X) are generally known compounds of organic chemistry.

The acylating agents which are furthermore required as starting materials for carrying out the process (a) according to the invention are generally defined by the formula (III). In this formula (III), X, Y, A and $Ar^1$ preferably represent those radicals which have already been mentioned in connection with the description of the substances, according to the invention, of the formula (I) as being preferred for these substituents.

$E^1$ preferably represents halogen, particularly chlorine or bromine, or an

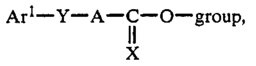

where X, Y, A and $Ar^1$ have the abovementioned meaning. The acylating agents of the formula (III) are generally known compounds of organic chemistry.

The 5-acylamido-1-aryl-pyrazoles which are required as starting materials for carrying out the process (b) according to the invention are generally defined by the formula (Ia). In this formula (Ia), $R^1$, X, Y, A, $Ar^1$ and $Ar^2$ preferably represent those radicals which have already been mentioned in connection with the description of the substances, according to the invention, of the formula (I) as being preferred for these substituents.

The 5-acylamido-1-aryl-pyrazoles of the formula (Ia) are compounds according to the invention and can be obtained with the aid of the processes (a), (c), (d) or (e) according to the invention.

The alkylating agents which are furthermore required as starting materials for carrying out the process (b) according to the invention are generally defined by the formula (IV). In this formula (IV), $R^{2-1}$ preferably represents straight-chain or branched alkyl having 1 to 12 carbon atoms, and particularly represents methyl, ethyl, n- or i-propyl and n-, i, s- or t-butyl.

$E^2$ preferably represents chlorine, bromine or iodine, methoxysulphonyloxy or p-toluenesulphonyloxy.

The alkylating agents of the formula (IV) are generally known compounds of organic chemistry.

The 5-acylamido-1-aryl-pyrazoles which are required as starting materials for carrying out the process (c)

according to the invention are generally defined by the formula (V). In this formula (V), $R^1$, $R^2$, X, A and $Ar^2$ preferably represent those radicals which have already been mentioned in connection with the description of the substances, according to the invention, of the formula (I) as being preferred for these substituents. $E^3$ preferably represents chlorine or bromine.

The 5-acylamido-1-aryl-pyrazoles of the formula (V) are known (cf. U.S. Pat. No. 4,363,804 or U.S. Pat. No. 4,614,533, supra, or they are the subject material of our own previous non-published German patent application DE-P No. 3,520,330 corresponding to U.S. application Ser. No. 866,638 filed May 22, 1986, now pending, supra, and can be obtained analogously to known processes (cf., for example, DE-OS (German published specification) No. 3,402,308; cf. also the preparation examples), for example when 5-amino-1-aryl-pyrazoles of the formula (II)

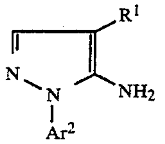

(II)

in which $R^1$ and $Ar^2$ have the abovementioned meaning, are acylated using acylating agents of the formula (XII),

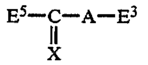

(XII)

in which $E^3$, X and A have the abovementioned meaning and $E^5$ represents a leaving group, such as, for example, halogen, particularly chlorine or bromine, or a

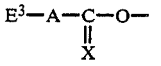

radical, where $E^3$, A and X have the abovementioned meaning, if appropriate in the presence of a diluent, such as, for example, dichloromethane, and if appropriate in the presence of an acid acceptor, such as, for example, pyridine, at temperatures between $-20°$ C. and $+120°$ C., and, if appropriate, subsequently alkylating, analogously to known processes and analogously to the process (b) according to the invention, in a 2nd stage using alkylating agents of the formula (IV), $$E^2—R^{2-1} \quad (IV)$$

in which $E^2$ and $R^{2-1}$ have the abovementioned meaning, if appropriate in the presence of a diluent, such as, for example, acetonitrile, and if appropriate in the presence of a catalyst, such as, for example, sodium methylate, at temperatures between 0° C. and 80° C.

The acylating agents of the formula (XII) are generally known compounds of organic chemistry.

The phenol or thiophenol derivatives which are furthermore required as starting materials for carrying out the process (c) according to the invention are generally defined by the formula (VI). In this formula (VI), $Ar^1$ and Y preferably represent those radicals which have already been mentioned in connection with the description of the substances, according to the invention, of the formula (I) as being preferred for these substituents, and Z preferably represents hydrogen or a sodium or potassium cation.

The phenol or thiophenol derivatives of the formula (VI) are generally known compounds of organic chemistry.

The 5-acylamido-1-aryl-pyrazoles which are required as starting materials for carrying out the process (d) according to the invention are generally defined by the formula (Id). In this formula (Id), $R^1$, $R^2$, X, A, $Ar^1$ and $Ar^2$ preferably represent those radicals which have already been mentioned in connection with the description of the substances, according to the invention, of the formula (I) as being preferred for these substituents.

The 5-acylamido-1-aryl-pyrazoles of the formula (Id) are compounds according to the invention and can be obtained with the aid of the processes (a), (b), (c) or (e) according to the invention.

The oxidizing agents which are furthermore required as starting materials for carrying out the process (d) according to the invention are generally defined by the formula (VII). In this formula (VII), $R^3$ preferably represents hydrogen, acetyl, trifluoroacetyl or optionally substituted benzoyl, such as, for example, 3-chlorobenzoyl or 4-nitrobenzoyl.

The oxidizing agents of the formula (VII) are generally known compounds of organic chemistry.

The 5-acylamido-1-aryl-pyrazoles which are required as starting materials for carrying out the process (e) according to the invention are generally defined by the formula (If). In this formula (If), $R^2$, X, Y, A, $Ar^1$ and $Ar^2$ preferably represent those radicals which have already been mentioned in connection with the description of the substances, according to the invention, of the formula (I) as being preferred for these substituents.

The 5-acylamido-1-aryl-pyrazoles of the formula (If) are compounds according to the invention and can be obtained with the aid of the processes (a), (b), (c) or (d) according to the invention.

The halogenating or nitrating agents which are furthermore required as starting materials for carrying out the process (e) according to the invention are generally defined by the formula (VIII). In this formula (VIII), $R^{1-1}$ preferably represents chlorine, bromine or nitro.

$E^4$ preferably represents a conventional leaving group, such as, for example, halogen and also phosphorus or sulphur-containing halogenated leaving groups. Suitable halogenating and nitrating agents are, for example, nitric acid, nitrating acid, sulphuryl chloride, phosphoroxy chloride, phosphoroxy bromide, phosphorus tribromide and similar generally conventional halogenating and nitrating agents.

The halogenating and nitrating agents of the formula (VIII) are generally known compounds.

Inert organic solvents are suitable as diluents for carrying out the process (a) according to the invention.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process according to the invention is, if appropriate, carried out in the presence of a suitable acid acceptor.

All conventional inorganic or organic bases are suitable as acid acceptor. These include, for example, alkali metal hydroxides, such as sodium hydroxide or potassium hydroxide, alkali metal carbonates, such as sodium carbonate, potassium carbonate or sodium bicarbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The process (a) according to the invention can also, if appropriate, be carried out in the presence of a suitable acylating catalyst. As such, acids such as sulphuric acid, hydrochloric acid, phosphoric acid, trifluoroacetic acid or Lewis acids, such as aluminum trichloride, boron trifluoride or iron trichloride, are preferably used.

The reaction temperatures can be varied within a relatively wide range when the process (a) according to the invention is carried out. In general, the process is carried out at temperatures between −20° C. and +150° C., preferably at temperatures between 0° C. and 100° C.

To carry out the process (a) according to the invention, 1.0 to 15.0 mols, preferably 1.0 to 5.0 mols, of acylating agent of the formula (III), if appropriate 1.0 to 3.0 mols, preferably 1.0 to 2.0 mols, of acid acceptor or, if appropriate, 0.1 to 3.0 mols, preferably 0.1 to 2.0 mols, of acylating catalyst are generally employed per mol of 5-amino-1-aryl-pyrazole of the formula (II). The reaction is carried out, and the reaction products of the formula (Ia) are worked up and isolated by conventional, known methods.

Inert organic solvents are also suitable as diluent for carrying out the process (b) according to the invention. The organic solvents mentioned for process (a) are preferably used.

The process (b) according to the invention can, if appropriate, also be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyl-ammonium-methyl sulphate, dimethyl-$C_{12}/C_{14}$-alkyl-benzylammonium chloride, tetrabutylammonium hydroxide, 15-crown-5, 18-crown-6, triethylbenzylammonium chloride, trimethylbenzylammonium chloride.

All inorganic and organic bases which can conventionally be used are suitable as acid acceptors for carrying out the preparation process (b). Alkali metal hydrides, hydroxides, amides, carbonates or bicarbonates, such as, for example, sodium hydride, sodium amide, sodium hydroxide, sodium carbonate or sodium bicarbonate, or, alternatively, tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

The reaction temperatures can be varied within a relatively wide range when the process (b) according to the invention is carried out. In general, the reaction is carried out at temperatures between −20° C. and +150° C., preferably at temperatures between 0° C. and +100° C., To carry out the process (b) according to the invention, 1.0 to 20.0 mols, preferably 1.0 to 15.0 mols, of alkylating agent of the formula (IV) and, if appropriate, 1.0 to 3.0 mols, preferably 1.0 to 2.0 mols, of acid acceptor and also 0.01 to 1.0 mol of phase transfer catalyst are generally employed per mol of 5-acylamido-1-aryl-pyrazole of the formula (Ia). The reaction is carried out, and the reaction products of the formula (Ib) are worked up and isolated in a generally conventional manner.

Inert organic solvents or aqueous systems are suitable as diluent for carrying out the process (c) according to the invention. The organic solvents mentioned for process (a) are preferably used. Polar organic solvents, such as methanol, ethanol, n-propanol, i-propanol, n-butanol, i-butanol, t-butanol, ethylene glycol, diethylene glycol, ethylene glycol monomethyl ether or monoethyl ether, diethylene glycol monoethyl ether or monoethyl ether, mixtures thereof with water or, alternatively, pure water are additionally preferred as diluent.

The process (c) according to the invention is, if appropriate, carried out in the presence of a suitable acid acceptor. As such, all inorganic or organic bases which can conventionally be used are suitable. The bases listed for process (b) are preferably used as acid acceptor.

The process (c) according to the invention can, if appropriate, alternatively be carried out in the presence of an acidic catalyst. Organic protonic acids, such as acetic acid or propionic acid, or strong mineral acids, such as hydrochloric acid, sulphuric acid or phosphoric acid, are preferably used.

The reaction temperatures can be varied within a relatively wide range when the process (c) according to the invention is carried out. In general, the reaction is carried out at temperatures between −20° C. and +120° C., preferably at temperatures between 0° C. and 100° C.

To carry out the process (c) according to the invention, 1.0 to 5.0 mols, preferably 1.0 to 3.0 mols, of phenol or thiophenol derivative of the formula (VI) and, if appropriate, 1.0 to 5.0 mols, preferably 1.0 to 3.0 mols, of acid acceptor or 0.001 to 2.0 mols, preferably 0.01 to 1.2 mols, of acidic catalyst are generally employed per mol of 5-acylamido-1-aryl-pyrazole of the formula (V). The reaction is carried out, and the reaction products of the formula (I) are worked up and isolated analogously to generally known processes.

Inert organic solvents are also suitable as diluent for carrying out the process (d) according to the invention.

Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide, are preferably used.

The process (d) according to the invention can, if appropriate, be carried out in the presence of an acid acceptor. As such, all organic and inorganic acid acceptors which can conventionally be used are suitable. Alkaline earth metal or alkali metal hydroxides, acetates or carbonates, such as, for example, calcium hydroxide, sodium hydroxide, sodium acetate or sodium carbonate, are preferably used.

The process (d) according to the invention can, if appropriate, be carried out in the presence of a suitable catalyst. As such, all catalysts, such as, particularly, metal salts, which are customarily conventional for such sulphur oxidations are suitable. Ammonium molybdate may be mentioned as an example in this connection.

The reaction temperatures can be varied within a relatively wide range when the process (d) according to the invention is carried out. In general, the reaction is carried out at temperatures between $-20°$ C. and $+70°$ C., preferably at temperatures between 0° C. and $+50°$ C., To carry out the process (d) according to the invention, 0.8 to 1.2 mols, preferably equimolar amounts, of oxidizing agent of the formula (VII) are generally employed per mol of 5-acylamido-1-aryl-pyrazole of the formula (Id) when it is desired to interrupt the oxidation of the sulphur at the sulphoxide stage. For oxidation to the sulphone, 1.8 to 3.0 mols, preferably double the molar amounts, of oxidizing agent of the formula (VII) are generally employed per mol of 5-acylamido-1-aryl-pyrazole of the formula (Id). The reaction is carried out, and the final products of the formula (Ic) are worked up and isolated by conventional and known processes.

All solvents which can conventionally be used for such electrophilic substitutions are suitable as diluent for carrying out the preparation process (e). The acids or mixtures, such as, for example, nitric acid, nitrating acid, sulphuryl chloride or nitrating acid, which are suitable as reagents are preferably used simultaneously as diluents. Inert organic solvents, such as, for example, glacial acetic acid or chlorinated hydrocarbons, such as methylene chloride, chloroform or carbon tetrachloride, are, if appropriate, also suitable as diluent.

The conventional catalysts for such reactions are also suitable as catalysts or reaction auxiliaries for carrying out the preparation process (e); acidic catalysts, such as, for example, sulphuric acid, iron-III chloride or other Lewis acids or acetic anhydride are preferably used.

The reaction temperatures can be varied within a relatively wide range when the preparation process (e) is carried out. In general, the process is carried out between $-50°$ C. and $+200°$ C., preferably between $-20°$ C. and $+150°$ C.

To carry out the preparation process (e), 1.0 to 10.0 mols, preferably 1.0 to 5.0 mols, of halogenating or nitrating agent of the formula (VIII) and, if appropriate, 0.1 to 10 mols of catalyst or reaction auxiliary are generally employed per mol of 5-acylamido-1-aryl-pyrazole of the formula (If). The reaction is carried out, and the reaction products of the formula (Ie) are worked up and isolated in a generally conventional manner.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Eme, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds in monocotyledon and dicotyledon cultures, such as, for example, soy beans, barley, wheat or corn.

The intermediates of the formula (V), too, have good herbicidal activity.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin5(4H)-one for combating weeds in sugar beet, and 4-amino6-(1,1-dimethylethyl)-3-methylthio-1,2,4-triazin-5(4H)-one for combating weeds in soy beans.

Mixtures with N,N-dimethyl-N'-(3-chloro-4-methylphenyl)-urea; N,N-dimethyl-N'-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; chloroacetic N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; 2-benzyloxyethyl, trimethylsilylmethyl or 2,2-diethoxyethyl 2-[4-(3,5-dichloropyrid-2-yloxy)-phenoxy]-propionate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; N-(1-ethylpropyl)-3,4-dimethyl-2,6-dinitroaniline; 0-(6-chloro-3-phenyl-pyridazin-4-yl) S-octyl-thiocarbonate; N,N-diisopropyl-S-(2,3,3-trichloroallyl)-thiolcarbamate; N-methyl2-(1,3-benzthiazol-2-yloxy)-acetanilide; exo-1-methyl-4-( 1-methylethyl)-2-(2-methylphenylmethoxy)-7-oxabicyclo(2,2,1)-heptane; 2-{4-[(3-chloro-5-(trifluoromethyl)-2-pyridinyl)-oxy]-phenoxy}-propionic acid or the ethyl ester thereof; 3,5-dibromo-4-hydroxy-benzonitrile; 2-[5-methyl-5-(1-methylethyl)-4-oxo-2-imidazolin-2-yl]-3-quinolinecarboxylic acid or 1-(3-trifluoromethyl-phenyl)-4-methylamino-5-chloropyridazone-(6) may be advantageous.

Some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and the use of the active compounds according to the invention follows from the examples below.

PREPARATION EXAMPLES

Example 1

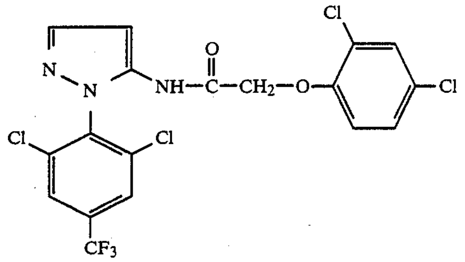

(Process a)

2.2 ml (0.0275 mol) of anhydrous pyridine and 6.7 g (0.027 mol) of 96.3 percent strength 2,4-dichlorophenoxyacetyl chloride are added successively to 8 g (0.027 mol) of 5-amino-1-(2,6-dichloro-4-trifluoromethylphenyl)-pyrazole (cf. U.S. Pat. No. 4,614,533, supra, in 60 ml of dichloromethane with stirring at 0° C. to 5° C. and the mixture is stirred for 16 hours at room temperature. The mixture is worked up by adding 100 ml of dichloromethane, washing successively with dilute hydrochloric acid, saturated sodium bicarbonate solution and saturated sodium chloride solution, drying the organic phase over magnesium sulphate and removing the solvent in vacuo. 12.7 g (94.3% of theory) of 5-(2,4-dichlorophenoxyacetamido)-1-(2,6-dichloro-4-trifluoromethylphenyl)-pyrazole of melting point 167° C.–180° C. are obtained.

Example 2

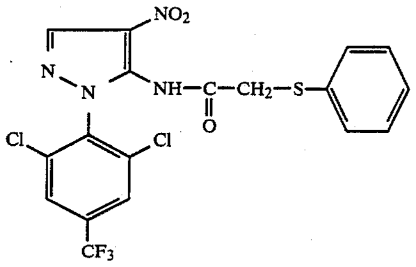

(Process c)

3.1 g (0.0282 mol) of thiophenol and 10 g (0.024 mol) of 5-chloroacetamido-4-nitro-1-(2,6-dichloro-4-tri-fluoromethyl-phenyl)-pyrazole dissolved in 50 ml of dry dimethoxyethane are added successively to 0.85 g (0.0283 mol) of 80 percent strength sodium hydride in 50 ml of dry dimethoxyethane under nitrogen at 15° C.-20° C.. After stirring for 3 hours, 25 ml of ethanol are added dropwise and the mixture is concentrated in vacuo. The oily residue is purified by chromatography (silica gel; eluant: dichloromethane). 9.5 g (81% of theory) of 4-nitro-5-(phenylthio-acetamido)-1-(2,6-dichloro-4-tri-fluoromethyl-phenyl)-pyrazole of melting point 98° C.-99° C. are obtained.

Example 3

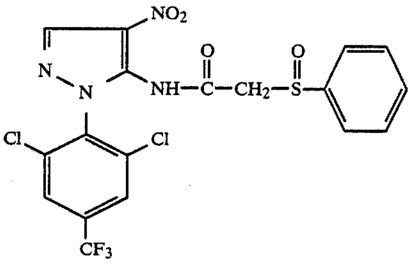

(Process d)

3.0 g (0.0061 mol) of 4-nitro-5-phenylthioacetamido-1-(2,6-dichloro-4-trifluoromethyl-phenyl)-pyrazole and 1.4 g (0.0073 mol) of 90 percent strength 3-chloroperbenzoic acid in 30 ml of dichloromethane are stirred for 16 hours at room temperature and filtered, the filtrate is washed successively with sodium bicarbonate-, sodium thiosulphate-solution, again with sodium bicarbonate solution and then with sodium chloride solution, dried over magnesium sulphate and freed of solvent in vacuo. 3.0 g (96.8% of theory) of 4-nitro-5-phenylsulphinylacetamido1-(2,6-dichloro-4-trifluoromethyl-phenyl)-pyrazole of melting point 108° C.-110° C. are obtained.

Example 4

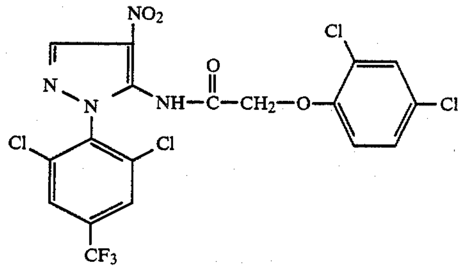

(Process e)

1.45 ml (0.0154 mol) of acetic anhydride and 0.60 ml (0.014 mol) of 98 percent strength nitric acid are added successively to 7.0 g (0.014 mol) of 5-(2,4-dichlorophenoxyacetamido)-1-(2,6-dichloro-4-trifluoromethyl-phenyl)-pyrazole in 30 ml of glacial acetic acid at about 150° C. After stirring for 20 hours, the mixture is concentrated in vacuo, the residue is taken up in 100 ml of dichloromethane and washed successively with saturated sodium bicarbonate solution and saturated sodium chloride solution. The organic phase is dried over magnesium sulphate and freed of solvent in vacuo. 8.6 g (81.6% of theory) of 5-(2,4-dichlorophenoxyacetamido)-4-nitro-1-2,6-dichloro-4-trifluoromethyl-phenyl)-pyrazole of melting point 155° C.-160° C. are obtained.

Example 5

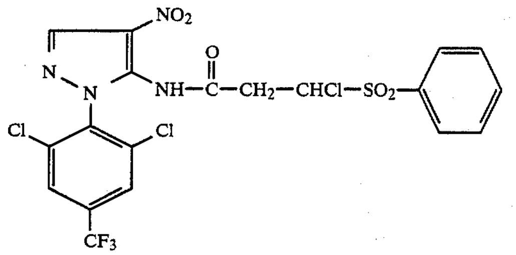

(Process a)

6.6 g (0.247 mol) of 3-chloro-3-phenylsulphonylpropionyl chloride and two drops of 96 percent strength sulphuric acid are added to 4 g (0.117 mol) of 5-amino-4-nitro- 1-(2,6-dichloro-4-trifluoromethyl-phenyl)-pyrazole in 30 ml of 1,2-dichlorobenzene and the mixture is heated for 6 hours at 100° C. The reaction mixture is freed of solvent in vacuo and separated by column chromatography using silica gel as carrier material and dihloromethane as eluent. 1.7 g (25.4 % of theory) of 5-(3-chloro-3-phenylsulphonylpropionylamido)-4-nitro-1-(2,6-dichloro-4-trifluoromethylphenyl)-pyrazole of melting point 122° C. are obtained.

The following 5-acylamido-1-aryl-pyrazoles of the general formula (I) are obtained in a corresponding fashion according to the general directions for the preparation:

TABLE 2
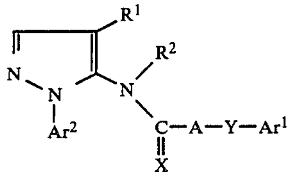
(I)
| Ex. No. | $R^1$ | $R^2$ | $-\overset{X}{\overset{\|}{C}}-A-Y-Ar^1$ | $Ar^2$ | Melting point °C. |
|---|---|---|---|---|---|
| 6 | H | H | 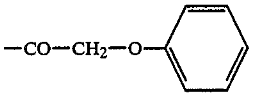 | 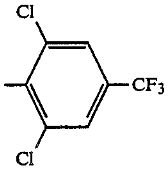 | 113–116 |
| 7 | $NO_2$ | H | 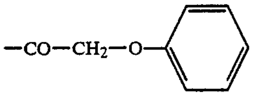 | 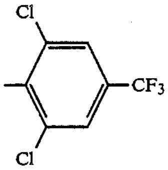 | 144–148 |
| 8 | $NO_2$ | H | 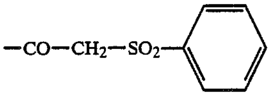 | 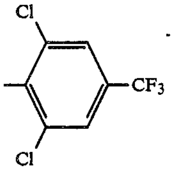 | 162–164 |
| 9 | $NO_2$ | H | 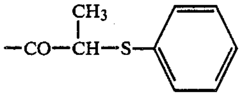 | 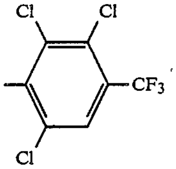 | |
| 10 | $NO_2$ | H | 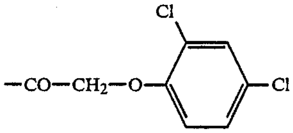 | 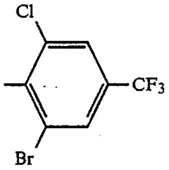 | 156–160 |
| 11 | $NO_2$ | H | 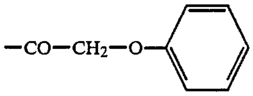 | 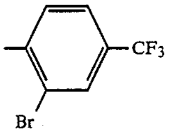 | 80–90 |
| 12 | H | H | 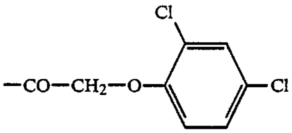 | 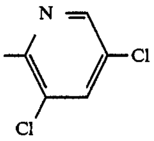 | 151 |
| 13 | H | H | 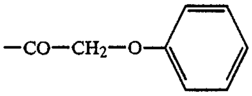 | 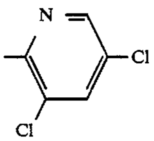 | 142–145 |

TABLE 2-continued
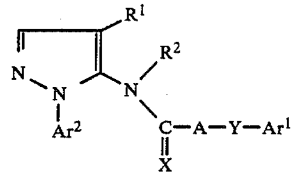
(I)
| Ex. No. | $R^1$ | $R^2$ | 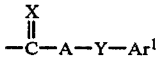 | $Ar^2$ | Melting point °C. |
|---|---|---|---|---|---|
| 14 | $NO_2$ | H | 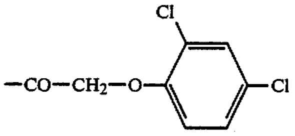 | 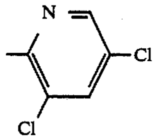 | 165 |
| 15 | $NO_2$ | H | 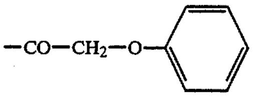 | 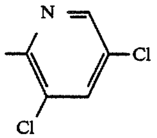 | 142 decomp. |
| 16 | H | H | 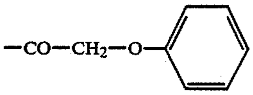 | 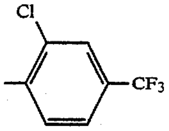 | 115–118 |
| 17 | H | H | 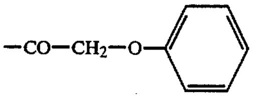 | 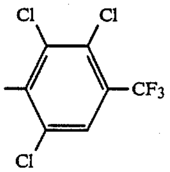 | 146–149 |
| 18 | H | H | 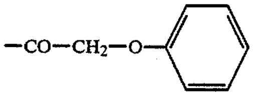 | 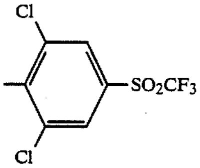 | 155–158 |
| 19 | H | H | 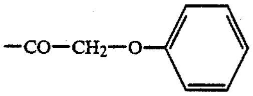 | 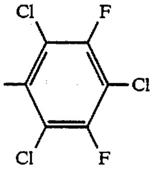 | 165–167 |
| 20 | $NO_2$ | H | 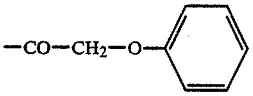 | 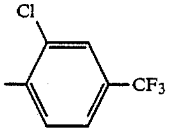 | 177–180 |
| 21 | $NO_2$ | H | 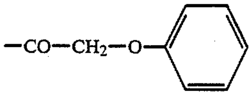 | 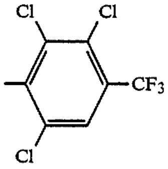 | 110–113 |

TABLE 2-continued
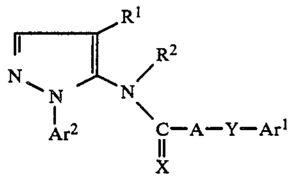
(I)
| Ex. No. | $R^1$ | $R^2$ | 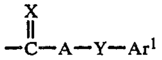 | $Ar^2$ | Melting point °C. |
|---|---|---|---|---|---|
| 22 | $NO_2$ | H | 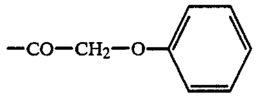 | 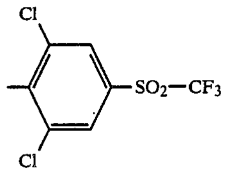 | 142–144 |
| 23 | $NO_2$ | H | 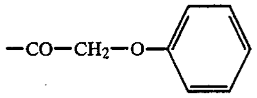 | 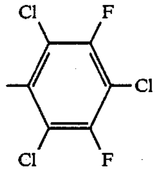 | 183–186 |
| 24 | H | H | 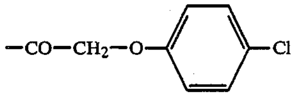 | 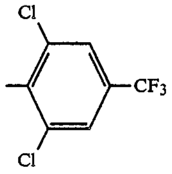 | 146–148 |
| 25 | H | H | 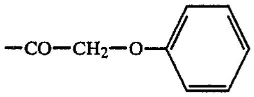 | 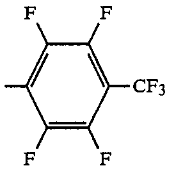 | 79–82 |
| 26 | $NO_2$ | H | 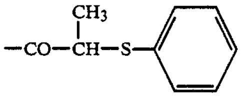 | 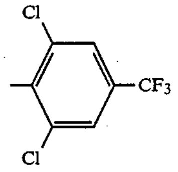 | 106–109 |
| 27 | $NO_2$ | H | 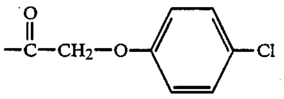 | 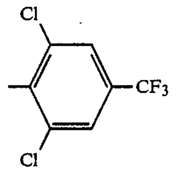 | 141–145 |
| 28 | $NO_2$ | H | 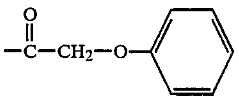 | 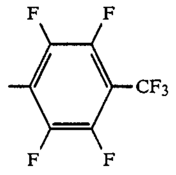 | 112–113 |

TABLE 2-continued
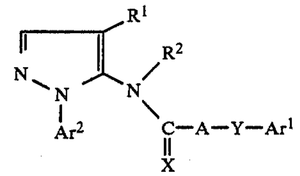
(I)
| Ex. No. | $R^1$ | $R^2$ | 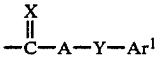 | $Ar^2$ | Melting point °C. |
|---|---|---|---|---|---|
| 29 | H | H | 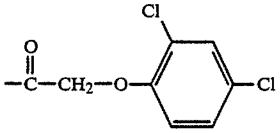 | 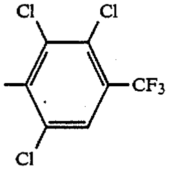 | 168–177 |
| 30 | $NO_2$ | H | 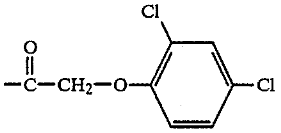 | 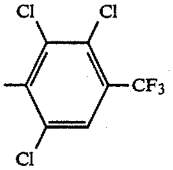 | 162–165 |
| 31 | $NO_2$ | H | 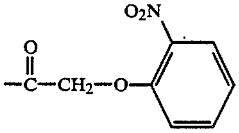 | 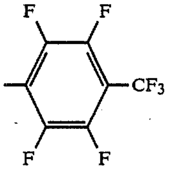 | 158–169 |
| 32 | $NO_2$ | H | 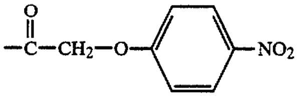 | 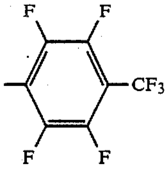 | 158–169 |
| 33 | H | H | 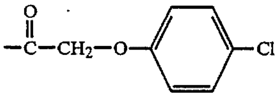 | 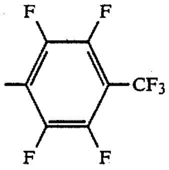 | 107–109 |
| 34 | H | H | 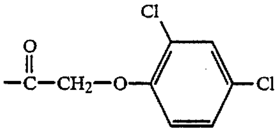 | 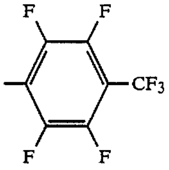 | 157–159 |
| 35 | $NO_2$ | H | 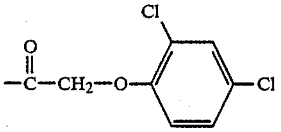 | 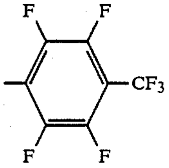 | 152–157 |

TABLE 2-continued

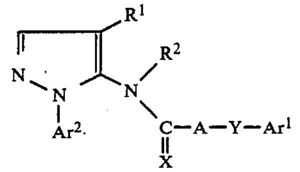

(I)

| Ex. No. | $R^1$ | $R^2$ | X ‖ —C—A—Y—$Ar^1$ | $Ar^2$ | Melting point °C. |
|---|---|---|---|---|---|
| 36 | $NO_2$ | H | 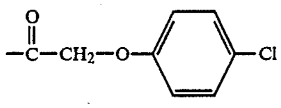 | 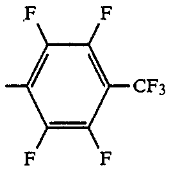 | 48-54 |
| 37 | H | H | 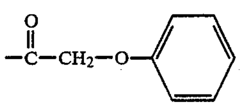 | 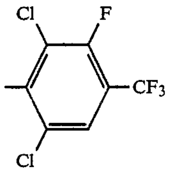 | 114-116 |

Preparation of the starting compounds

Example V-1

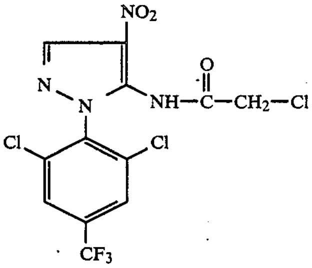

1.03 ml (0.011 mol) of acetic anhydride and 0.56 ml (0.013 mol) of 98 percent strength nitric acid are added successively to 4.2 g (0.011 mol) of 5-chloroacetamido-1-(2,6-dichloro-4-trifluoromethyl-phenyl)-pyrazole in 20 ml of glacial acetic acid at 15° C. After stirring for 6 hours, the mixture is concentrated in vacuo, the residue is taken up in 100 ml of dichloromethane and washed successively with saturated sodium bicarbonate solution and saturated sodium chloride solution. The organic phase is dried over magnesium sulphate and freed of solvent in vacuo. 4.1 g (89% of theory) of 5-chloroacetamido-4-nitro-1-(2,6-dichloro-4-trifluoromethylphenyl)-pyrazole of melting point 130° C.-133° C. are obtained.

The following are obtained analogously:

Example V-2

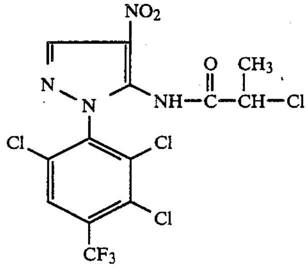

Melting point: 50° C.-52° C.

Example V-3

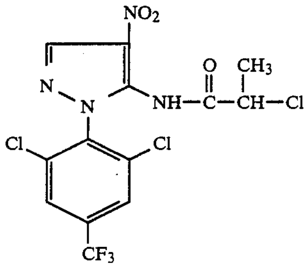

Melting point: 53°-56° C.

Example V-4

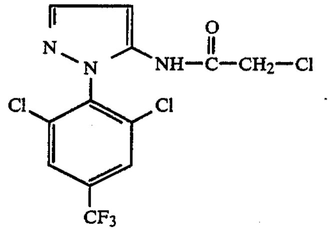

10.8 g (0.102 mol) of anhydrous sodium carbonate and 4.1 ml (0.051 mol) of chloroacetyl chloride are added to 5 g (0.017 mol) of 5-amino-1-(2,6-dichloro-4-trifluoromethylphenyl)-pyrazole in 50 ml of dichloromethane with stirring at 15° C.-20° C. After stirring for 16 hours, 100 ml of dichloromethane and 100 ml of water are added. The organic phase is separated off, washed with saturated sodium chloride solution and dried over magnesium sulphate. After removal of the solvent in vacuo, 5.7 g (90.5% of theory) of 5-chloroacetamido-1-(2,6-dichloro-4-trifluoromethylphenyl)-pyrazole of melting point 149° C.-150° C. are obtained.

The following are obtained analogously:

Example V-5

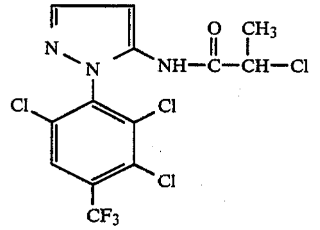

Melting point: 53° C.-55° C.

Example V-6

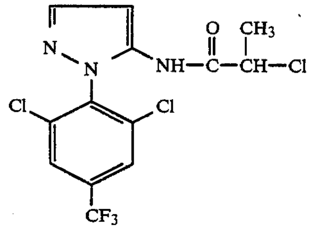

Melting point: 55°-57° C.

USE EXAMPLES

In the following use examples, the compound described below was employed as comparison substance:

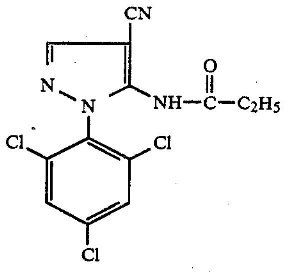

(A)

4-Cyano-5-propionamido-1-(2,4,6-trichlorophenyl)-pyrazole (known from DE-OS (German Published Specification) 3,226,513)

EXAMPLE A

Pre-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to preparation Examples 4 and 7 exhibit a clearly superior activity and useful-plant selectivity compared to the comparison substance (A).

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)

100% = total destruction

In this test, for example, the compounds according to preparation Examples 2, 4, 7 and 10 exhibit a clearly superior activity and useful-plant selectivity compared to the comparison substance (A).

It will be appreciated that the instant specification and examples are set forth by way of illustration and not limitation, and that various modifications and changes may be made without deporting from the spirit and scope of the present invention.

We claim:

1. A 5-acylamido-1-arylpyrazole of the formula

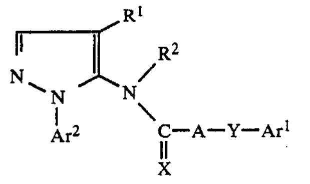

in which $R^1$ represents hydrogen, nitro, fluorine, chlorine, bromine or iodine, $R^2$ represents hydrogen or straight-chain or branched alkyl having 1 to 12 carbon atoms, X represents oxygen or sulphur, Y represents oxygen, sulphur, a sulphinyl group or a sulphonyl group, A represents a straight-chain or branched, optionally singly or multiply, identically or differently, halo-substituted alkylene bridge having 1 to 6 carbon atoms, $Ar^1$ represents phenyl, 2-pyridyl, 3-pyridyl, 4-pyridyl, 2-pyrimidyl, 4-pyrimidyl, 5-pyrimidyl, 3-pyridazinyl, 4-pyridazinyl, pyrazinyl or s-triazinyl, each optionally substituted by at least one of halogen, cyano, nitro, in each case straight-chain or branched alkyl, alkoxy or alkoxy carbonyl having 1 to 4 carbon atoms in each of the alkyl parts, in each case straight-chain or branched haloalkyl or haloalkoxy having 1 to 4 carbon atoms and 1 to 9 identical or different halogen atoms in each case, or a $-S(O)_m-R^4$ radical, $R^4$ represents amino, in each case straight-chain or branched alkyl, alkylamino, dialkylamino or haloalkyl having 1 to 4 carbon atoms in each of the individual alkyl parts and, in the case of haloalkyl, having 1 to 9 identical or different halogen atoms and m represents a number 0, 1 or 2 and $Ar^2$ represents phenyl, 2-pyridyl, 3-pyridyl or 4-pyridyl, each optionally substituted by those substituents mentioned for $Ar^1$.

2. A 5-acylamido-1-aryl pyrazole according to claim 1, in which $R^1$ represents hydrogen, nitro, chlorine or bromine, $R^2$ represents hydrogen or straight-chain or branched alkyl having 1 to 8 carbon atoms, A represents a bridging member of the formula

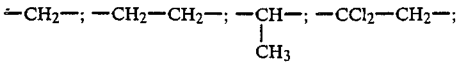

-continued

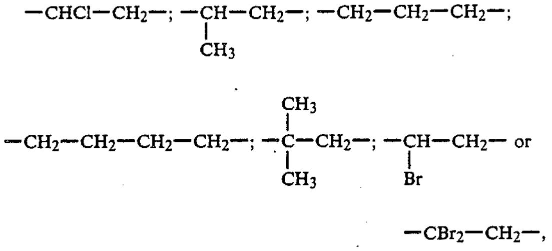

$Ar^1$ represents phenyl, 2-pyridyl, 3-pyridyl, 4-pyridyl, 2-pyrimidyl, 4-pyrimidyl, 5-pyrimidyl, 3-pyridazinyl, 4-pyridazinyl, pyrazinyl or s-triazinyl, each optionally substituted by at least one of cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a $-S(O)_m-R^4$ radical, where $R^4$ represents amino, methylamino, ethylamino, dimethylamino, diethylamino, fluorodichloromethyl, difluoromethyl, tetrafluoroethyl, trichloroethyl, trifluoromethyl, difluorochloromethyl, methyl or ethyl and m represents a number 0, 1 or 2 and $Ar^2$ represents phenyl, 2-pyridyl or 4-pyridyl, each optionally substituted by those substituents mentioned for $Ar^1$.

3. A compound according to claim 1, wherein such compound is 5-(2,4-dichlorophenoxyacetamido)-4-nitro-1-(2,6-dichloro-4-trifluoromethyl-phenyl)-pyrazole of the formula

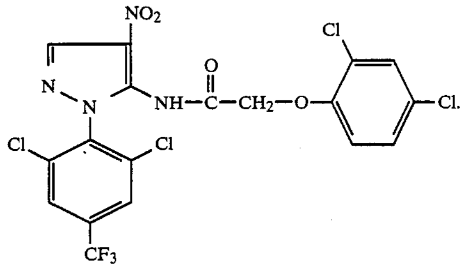

4. A compound according to claim 1, wherein such compound is 5-phenoxyacetamido-4-nitro-1-(2,6-dichloro-4-trifluoroemthyl-phenyl)-pyrazole of the formula

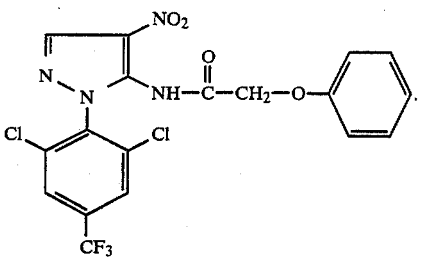

5. A compound according to claim 1, wherein such compound is 5-phenoxyacetamido-4-nitro-1-(2-chloro-4-trifluoromethyl-phenyl)-pyrazole of the formula

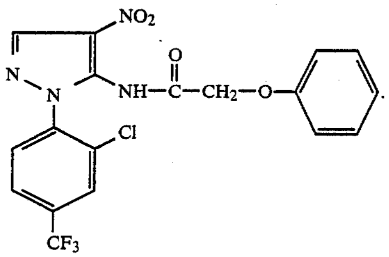

6. A compound according to claim 1, wherein such compound is 5-phenoxyacetamido-4-nitro-1-(2,3,6-trichloro-4-trifluoromethyl-phenyl)-pyrazole of the formula

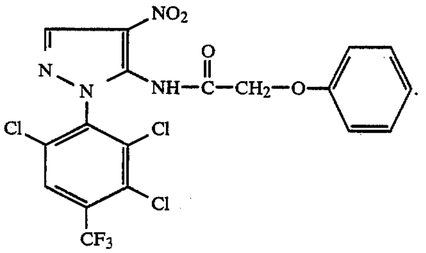

7. A compound according to claim 1, wherein such compound is 5-phenoxyacetamido-4-nitro-1-(2,3,5,6-tetrafluoro-4-trifluoromethyl-phenyl)-pyrazole of the formula

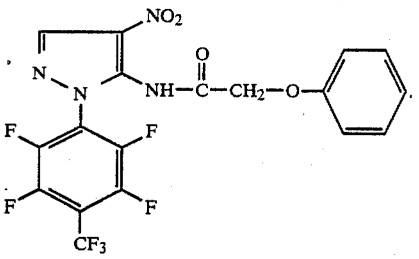

8. A compound according to claim 1, wherein such compound is 5-(2-nitro-phenoxyacetamido)-4-nitro-1-(2,3,5,6-tetrafluoro-4-trifluoromethyl-phenyl)-pyrazole of the formula

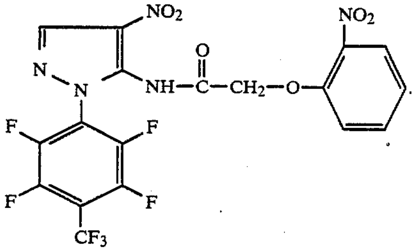

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is 5-(2,4-dichlorophenoxyacetamido)-4-nitro-1-(2,6-dichloro-4-trifluoromethyl-phenyl)-pyrazole, 5-phenoxyacetamido-4-nitro-1-(2,6-dichloro-4-trifluoromethyl-phenyl)-pyrazole, 5-phenoxyacetamido-4-nitro-1-(2-chloro-4-trifluoromethyl-phenyl)-pyrazole, 5-phenoxyacetamido-4-nitro-1-(2,3,6-trichloro-4-trifluoromethyl-phenyl)-pyrazole, 5-phenoxyacetamido-4-nitro-1-(2,3,5,6-tetrafluoro-4-trifluoromethyl-phenyl)-pyrazole or 5-(2-nitro-phenoxyacetamido)-4-nitro-1-(2,3,5,6-tetrafluoro-4-trifluoromethyl-phenyl)-pyrazole.

* * * * *